United States Patent [19]

Brinton, Jr. et al.

[11] Patent Number: 4,725,435

[45] Date of Patent: Feb. 16, 1988

[54] **VACCINE COMPOSITION FOR IMMUNIZATION AGAINST URINARY TRACT INFECTION CAUSED BY *E. COLI***

[75] Inventors: Charles C. Brinton, Jr.; Peter C. Fusco, both of Pittsburgh, Pa.

[73] Assignee: Bactex, Inc., Pittsburgh

[21] Appl. No.: 875,473

[22] Filed: Jun. 18, 1986

[51] Int. Cl.⁴ ............................................ A61K 39/108
[52] U.S. Cl. .................................... 424/92; 424/88; 424/85; 424/87; 436/547
[58] Field of Search ................ 424/88, 92, 85, 87; 436/547

[56] References Cited

U.S. PATENT DOCUMENTS 4,454,116  6/1984  Brinton .................................. 424/92
4,454,117  6/1984  Brinton .................................. 424/92
4,606,919  8/1986  Stojkonic et al. ..................... 424/92

FOREIGN PATENT DOCUMENTS 0161095  11/1985  European Pat. Off. .

*Primary Examiner*—John Kight
*Assistant Examiner*—Garnette D. Draper
*Attorney, Agent, or Firm*—Omri M. Behr

[57] ABSTRACT

There is provided a vaccine material capable of providing substantial levels of protection against urinary tract infection caused by *Escherichia coli*. The protecting means comprises pili of organisms having pili of the same pilic family as those on the infecting organism. Protection is given by administering the pili to the subject to be protected.

10 Claims, No Drawings

VACCINE COMPOSITION FOR IMMUNIZATION AGAINST URINARY TRACT INFECTION CAUSED BY E. COLI

BACKGROUND OF THE INVENTION

Escherichia coil is a ubiquitous pathogen of man and animals causing a wide variety of diseases of clinical and economic importance. E. coli is the most frequent cause of urinary tract infections (UTI) causing the symptoms of acute and chronic cystitis, pyelonephritis, and asymptomatic bacteriuria (ABU). A general approach to this problem is disclosed in U.S. Pat. Nos. 4,454,116 and 4,454,117 to Brinton.

SUMMARY OF THE INVENTION

It has been found that UTI infections are caused by E. coli organisms carrying pili belonging to three pilic families, namely, Type 1, P and p (See Race & Sanger, Blood Groups in Man, 6th. Ed., 1975, Blackwell, Oxford; Naiki & Kato, Vox Sanguinis, 37, 30, 1979). In particular, it has been found that the majority of infections are caused by organisms having one or more pili belonging to at least one of seven pilic groups within the Type 1 family, four pilic groups within the P family and two pilic groups within the p family.

It should be borne in mind that the important factor in selecting an effective vaccine composition is not whether the protecting organism forms antibodies against the infecting organism but rather whether the protecting pili form antibodies that react with the pill on the infecting organisms. This principle is an important one since there is not always a direct correlation between the pili and the organisms. Thus, different strains may carry pili belonging to not only the same family but belonging to groups within that family. Thus, there are provided vaccine compositions capable of raising the antibody level of the subject to a level sufficient to protect against UTI infection caused by organisms of a first (infecting) group of strains of E. coli comprising a pharmaceutically acceptable carrier and pili, suitably separated from other E. coli organism components, derived from at least one member each selected from a second (protecting) group of strains of E. coli organisms, wherein the cells of organisms of the first (infecting) group are agglutinated by serum containing antibodies against said pili from said second (protecting) group, wherein the first group consists of strains which may be the same or different from the strains of the second group. Said second group consists of strains of piliated E. coli organisms having pili of the Type 1, P, and p families. In particular, the organisms giving rise to pili of the Type 1 family are:

| Culture No. | ATCC No. |
|---|---|
| B9 | 31702 |
| Bam | 67053 |
| RD | 53507 |
| 27 | 53498 |
| H/T-1 | 31705 |
| 51 | 53508 |
| Br | 53506 |

The P family pili are derived from organisms designated as 46056, 28418, 13774, C8, 31920 (ATCC #53501, 53504, 53505, 53503, 53502).

The organisms giving rise to pili of the p family comprise two further subgroups $p_1$ Culture No. 1910, ATCC #53499 and $p_2$ Culture No. 750, ATCC #53500.

The important designating factor in the design of the vaccines of the present invention is not the identity of the organism giving rise to the particular protecting pili. Thus, the designation of the strains giving rise to these pili is merely a matter of identifying convenience and should in no way be considered as limiting the invention to pili specifically derived from the named strains. It is considered that the present invention extends to pili derived from any strains which generate pili which fall within the above named Type 1, P and p families and furthermore, will generate antibodies which would cross react with or agglutinate the pili derived from the above named strains.

DESCRIPTION OF THE PREFERRED EMBODIMENTS

Isolation and characterization of organisms

E. coli organisms may express pili belonging to one or more pilic families. In the initial isolation characterization phase, the parent culture is grown on minimum glucose agar and casamino acid-yeast extract (CAYE) agar at 37° C. to ensure expression of Type 1 as well as P and p family pili and the initial colonies inspected, screened and cultured under conditions, set forth in detail hereinbelow particularly conducive to the expression of pili of a particular family. Thus, colonies expressing pili which agglutinate guinea pig red blood cells but where such agglutination is inhibited by the presence of D-mannose are classified as belonging to the Type 1 family. They are then grown on minimal glucose agar base medium in liquid broth. The pili which agglutinate P human red blood cells or latex coated with tetraglobosyl digalactoside, where said agglutination is not inhibited by D-mannose and further, which do not agglutinate gP (guinea pig) red blood cells are classified as P pili. Pili which agglutinate p human red blood cells and do not glutinate 6P red blood cells and further, whose agglutination against p human red blood cells is not inhibited by D-mannose are classified as belonging to the p family. Once isolated and characterized however, the growth and purification steps of strains belonging to both the P and p families is the same, suitably they are grown on CAYE agar.

The physical characteristics of Type 1 family pili may be summarized as follows. The pili rod morphology describes rigid rods approximately 6nm in diameter of helically arranged identical protein subunits. The subunits have a molecular weight range of between about 17.1 and 17.7 K daltons and will dissolve at a pH above 7.2 in solutions of ionic strength up to about $0.1\mu$. They have a UV absorption maximum at 280 mu and an $\epsilon$ of 0.3 ABS/mg/ml. They require acid and heat to enter a SDS polyacrylamide gel.

The P family pili have a molecular weight range of 17 to 17.5 K daltons and the p pili have a molecular weight of 15 KD ($p_1$) to through 16.5 KD ($p_2$). Both have a rod morphology of flexible helical rods with a tendency to unwind to provide very thin flexible fibers. The rod diameter is of the order of 6 nm. P and p family pili are soluble in 0.063M aqueous ethanolamine at a pH of between about 10.6 to about 11 and they may be precipitated from such a solution by the addition of between 20 and 30% by weight aqueous ammonium sulfate.

In view of the rather different solubility characteristics, coupled with the fact that aqueous ethanolamine of the foregoing strength is not pharmacologically acceptable, a vaccine comprising pili of the Type 1, P and p families will of neccessity, comprise components which are substantially soluble in physiological saline (suitably PBS) and those which are not. Provided that the insoluble portion is sufficiently finely divided to be injectable, this creates no problems.

The pili may be administered orally—say, in capsule form—or by injection—that is to say, subcutaneous, intradermal, or intramuscular injections. Where the mode of administration is by injection, since the pili are solid, any pharmaceutically acceptable suspending medium may be employed. It has been found especially useful to employ phosphate buffer, suitably containing merthiolate, as the vehicle or suspending medium. It is preferred to use 0.0005–0.1, most suitably 0.004M phosphate buffer, at ionic strength containing 0.0005 to $0.1\mu$, and, suitably 0.01% merthiolate. The concentration of pili in the vehicle is not critical. The sole criterion of desirability being that the pili shall be sufficiently finely divided to provide a suspension which meets generally accepted standards of syringeability. A concentration of 1–30, preferably about 20 mg of pilus protein per 10 ml of suspending medium is especially suitable.

It is generally preferred to administer the vaccine composition in more than one dose separated by a predetermined time factor. This time factor is selected to permit the formation of an adequate titer of antibodies to the pili in the injected subject. It has been found suitable to administer the vaccine composition at least once, preferably at 60 and again at 30 days pre-infection.

Since there are no local or systemic toxic effects engendered by the injection of vaccine, there appear to be no upper limits to the dosage administered. It has been found suitable, however, to administer between 1 and 100 micrograms of pili per kilogram of body weight, most suitably about 20 micrograms per kilogram of body weight per injection.

The foregoing amounts refer to total pili. Thus, if 10 different pili were utilized, the amount of each would be between about 0.07 and 7.5 micrograms per kilogram. Utilization of amounts closer to the high end of the range is to be preferred.

While it is preferable to provide a vaccine containing pili from each of the designated strains, a certain measure of protection is provided by a vaccine containing at least one member of each pilus family.

Sera containing antibodies against pili from strains designated above as belonging to the second group were utilized to test for the agglutination of cells derived from clinical organisms found in patients with various forms of UTI. These cross reactivities are set forth in Table 1 below which is directed to cross reactivity with Type 1 family pili and in Table 2 which is directed to cross reactivity with P and p family pili.

EXPLANATION OF TABLES

Among the various kinds of pili on *E. coli* strains, pilus families can be defined using physico-chemical characteristics, adhesion specificities, or antigenic relationships (serological specificities) but they are most usually defined by their adhesion specificities. Within a given family, serological variations may occur among pili, so that they can be further grouped into serotypes. This grouping is most conveniently and meaningfully done using antisera made against purified pili. For example, a single antiserum made against one member of the family can be shown to cross-react with or agglutinate pili from every type within the family at a certain titer. If, however, that single antiserum is allowed to react with another pilus in the family of different type (to remove antibodies to the family-specific antigenic determinants) then that absorbed antiserum will react only with other members of its type and not with family members belonging to other types. Sera against pili of the same type will cross-react at high titer while pili in the same family but of different type will cross-react at a significantly lower titer. It is these type-specific antibodies rather than family-specific antibodies that provide protection against disease, as shown in both human and animal experiments in a number of different diseases. Unless antibodies to all the types important in a disease are produced by vaccination complete protection may not be obtained. It follows then that each pilus type important in disease should be represented in the vaccine. The unique feature of the vaccine described here in is this type-specific representation, as defined by the typing strains listed but not excluding use of other members of a type.

The serological typing of three *E. coli* pilus families prevalent on urinary tract strains is shown herein. The cross-reactivity tables define the different serotypes. The frequency tables define the frequency of occurrence of the different serotypes on strains isolated from urinary tract infections. Since disease-protective antibodies are type-specific, the breadth of protection to be expected from a pilus vaccine is approximately equal to the percentage of naturally occurring strains which bear pilus types included in the vaccine.

SEROLOGICAL CROSS-REACTIVITY TABLE AMONG P PILUS TYPES PURIFIED FROM *ESCHERICHIA COLI* STRAINS ISOLATED FROM URINARY TRACT INFECTIONS
(Enzyme-linked immunoassay titers. Unabsorbed sera.)

| Purified pili | Antisera | | | | | | | |
|---|---|---|---|---|---|---|---|---|
| | 35000 | 46056 | 28418 | 13774 | 31920 | P75 | C7 | C8 |
| 35000 | $A_{6544}$ | $A_{4322}$ | 101 | 450 | 450 | 180 | 15 | 150 |
| 46046 | $A_{2582}$ | $A_{5488}$ | 96.7 | 650 | 87.5 | 125 | 119.1 | 125 |
| 28418 | 24.5 | 85 | $B_{2500}$ | 14 | 12 | 25.5 | 18.6 | 400 |
| 13774 | 150 | 130.5 | 544 | $C_{3205.9}$ | 67.6 | 262 | 312 | 440 |
| 31920 | 83 | 272 | 47.5 | 105 | $D_{5691}$ | $D_{4914}$ | $D_{690}$ | 40 |
| P75 | 368 | 416 | 74 | 195 | $D_{4960}$ | $D_{6500}$ | $D_{1625}$ | 250 |
| C7 | 475 | 46.1 | 21.8 | 36.5 | $D_{4681}$ | $D_{1625}$ | $D_{6046}$ | 212.5 |
| C8 | 38.6 | 133 | 48.3 | 70 | 40 | 5.7 | 12.5 | $E_{5500}$ |

$A, B, C, D, E$ represent P pilus types.

TABLE III

FREQUENCY OF P PILUS SEROTYPES ON STRAINS OF *E. COLI* ISOLATED FROM URINARY TRACT INFECTIONS AND BEARING P PILI AS DETERMINED BY ADHESION ASSAY
(Summary Table)

| Source of Isolate | P Pilus Type | | | | |
|---|---|---|---|---|---|
| | A | B | C | D | E |
| Asymptomatic bacteruria | 33% | <6% | 20% | 33% | 13% |
| Cystitic | 38% | 6% | 13% | 31% | 25% |
| Pyelonephritic | 36% | <5% | 9% | 59% | 9% |

Types A and D cover 68% of all strains.
Types A, C, D, E cover 73% of all strains.

TABLE IV

SEROLOGICAL CROSS-REACTIVITY TABLE AMONG p PILUS TYPES PURIFIED FROM *ESCHERICHIA COLI* STRAINS ISOLATED FROM URINARY TRACT INFECTIONS
(Enzyme-linked immunosorbent assay. Unabsorbed sera.)

| Purified pilus | Antisera | | |
|---|---|---|---|
| | 1910 | 3556 | 750 |
| 1910 | $^A$2800 | 1300 | 7 |
| 3556 | 2400 | 1640 | 7 |
| 750 | 29 | — | $^B$2800 |

$^{A, B}$represent p pilus types.

TABLE V

SEROLOGICAL CROSS-REACTIVITY TABLE AMONG THE DIFFERENT TYPE 1 PILUS TYPES PURIFIED FROM *ESCHERICHIA COLI*
(Enzyme linked immunosorbent assay.
Homologous titers normalized to 100%. Type-specific antisera.)

| PILI | SERA | | | | | | |
|---|---|---|---|---|---|---|---|
| | B9 | Bam | RD | H/T-1 | 51 | Br | 27 |
| B9 | 100 | −0.4 | 2.1 | 1.1 | 5.6 | 0.3 | −0.7 |
| Bam | 21.2 | 100 | 0.6 | 5.9 | 6.8 | 2.8 | 0.5 |
| RD | 55.3 | 3.2 | 100 | 3.0 | 17.7 | 18.6 | −0.3 |
| H/T-1 | 18.1 | 3.6 | 0.2 | 100 | 3.0 | 3.9 | 10.7 |
| 51 | 50.5 | 6.4 | 6.3 | 4.0 | 100 | 1.4 | 0.7 |
| Br | 15.2 | 27.6 | 10.6 | 5.8 | 6.0 | 100 | 0.0 |
| 27 | 16.1 | 2.8 | 0.7 | 52.3 | 4.4 | 4.8 | 100 |

TABLE VI

FREQUENCY OF TYPE 1 PILUS SEROTYPES ON *ESCHERICHIA COLI* STRAINS ISOLATED FROM URINARY TRACT PATHOGENS AND CLONED TO EXPRESS PILI IN THE TYPE 1 FAMILY

| STRAIN | PILUS TYPE | | | | | | |
|---|---|---|---|---|---|---|---|
| | B9 | Bam | RD | H/T-1 | 51 | Br | 27 |
| B9 | 4+ | — | — | — | — | — | — |
| E25 | 4+ | — | — | — | — | — | — |
| B7a | 4+ | — | — | — | — | — | — |
| Bam | — | 4+ | — | — | — | — | — |
| E28 | — | 3+ | — | — | — | — | — |
| RDEC | 1+ | — | 4+ | — | — | — | — |
| TD225 | 3+ | — | 4+ | — | — | — | — |
| H10407 | — | — | — | 4+ | — | — | 4+ |
| 51301 | — | — | — | — | 4+ | — | — |
| Br11 | — | 3+ | — | — | — | 4+ | — |
| 27052 | — | — | — | 3+ | — | — | 4+ |
| C3 | 4+ | — | — | — | — | — | — |
| 88524 | 2+ | — | 4+ | — | — | — | — |
| 18309 | — | — | — | 3+ | — | — | 4+ |
| 43761 | 4+ | — | 4+ | — | — | — | — |
| 54933 | — | — | — | — | 4+ | — | — |
| 86343 | — | 2+ | — | — | — | — | — |
| C18 | — | 2+ | — | — | — | 2+ | — |
| C47 | — | — | — | 3+ | — | — | — |
| C48 | 3+ | — | 4+ | — | — | 2+ | — |
| C49 | 3+ | — | — | — | — | — | — |
| C50 | — | — | — | 3+ | — | — | 4+ |
| C51 | — | — | — | 3+ | — | — | 4+ |
| C52 | — | — | — | 3+ | — | — | 4+ |

EXAMPLE I

Preparation of *Escherichia Coli* Pili (Type 1 Family)

A culture prepared by resuspending piliated phase colonies growing on minimal glucose agar base medium in a liquid Z broth (1% Bactotryptone, 0.8% NaCl, 0.1% yeast extract, 0.1% glucose) medium was used to inoculate trays containing the same growth medium solidified with agar. After overnight incubation at 37° C., the confluent bacterial growth was suspended in 0.01 molar phosphate buffered saline pH 7.0. About 20 milliliters of buffer was used to suspend the growth from one tray which dimensions were approximately 30 cm × 40 cm. The resuspended growth was blended, 200 milliliters at a time, at 14,000 rpm for 5 minutes in the 400 milliliter cup of a Sorvall OM-Nimixer in order to remove pili from the cells. Cells were then removed by centrifugation at 10,000 times G for 20 minutes and the supernatant liquid was retained. The pili were then crystallized by the addition of magnesium chloride ($MgCl_2$) to 0.1 molar. After the crystals formed, they were removed from suspension by centrifugation at 20,000 times G for 60 minutes, and the pellet was retained. The pellet containing the pilus crystals were redissolved in 0.004 molar phosphate buffer pH 7.02 (without saline. The suspension was clarified by centrifugation at 20,000 times G for 60 minutes and the supernatant liquid was retained. The cycle of crystallization, centrifugation, redissolution, and centrifugation was repeated 2 to 4 times to obtain the purified pilus suspension.

EXAMPLE II

Bulk Vaccine Preparation (a) High speed blending with Sorvall Omnimixer at 14,000 rpm for 10 minutes with 100 ml aliquots in a 200 ml cup, broke up pilus aggregates and sheared the rods 0.01% merthiolate was added as a preservative.

Removal of Flagella

Cycled solubilized pili preparations were adjusted to pH 12-3 by addition of 1N sodium hydroxide. After 30 minutes, at room temperature with occasional stirring, the pili were precipitated by addition of 10% (u/v) saturated ammonium sulphate followed by centrifugation at 20,000G for 30 minutes leaving dissociated flagella subunits in the supernate.

The precipitated pili were resolubilized in phosphate buffer (0.004 M).

The pili of the Type 1 family which are prepared in accordance with the foregoing procedure include pili prepared from the following strains B9, Bam, RD, 27 H/T-1, 51 and Br.

EXAMPLE III

Preparation of *Escherichia Coli* Pili (P and p Family)

Growth

Because of subtle differences, colonial morphology could best be detected in 10-14 hour cultures. Clones were maintained by continuous subculture every 12 hours on CAYE agar. Five to 6 colonies were picked to avoid selecting atypical mutants. Furthermore, growth in liquid media severely depleted the cultures of P and p piliated cells. Therefore, cultures for the inoculation of large growth trays (10½ × 15½ × 1 inch) had to be prepared on solid media both using CAYE agar. Growth for inoculation was harvested off CAYE agar in petri dishes using 7.5 ml of 0.7% casamino acids per dish and scraping the agar surface with a bent glass rod. The suspended growth was then pipetted out of the dish and used to inoculate 2 large growth trays, 2-3 ml per tray. After inoculation, the trays were covered with tightly fitted aluminum lids and incubated for 19-21 hours at 37° and 70% relative humidity in a dedicated floor model humidified incubator located in the adjacent room.

After incubation, the growth trays were returned to the vaccine facility for harvesting. Trays were inspected visually for contamination. Cultures were harvested with the addition of 5-8 ml harvest buffer using 0.063M ethanolamine in pH 10.0-12, using a clean glass plate to scrape the growth off the agar surface. Suspended growth was aspirated into a sterile flask and kept on ice until the entire day's harvest was collected. The pooled harvest was then treated as described in the following section.

Isolation of P and p Pili

To remove pili from the cells, the harvest suspension was blended in 200 ml portions in an ice chilled cup using the Sorvall Omnimixer. Each portion was blended for 2' at 9,000-10,000 rpm, as determined by 3 to 4 readings with a tachometer. Approximately half of an 80 tray harvest was blended and centrifuged before blending the remaining half. The blended harvest was centrifuged at 9,000 g for 10 minutes to remove the cells. The cell pellets were discarded.

Supernatants of blended cultures were pooled and the volume measured. Crystalline ammonium sulfate was added slowly to 20-30% saturation with constant stirring. Streaming birefringence was immediately visable. The preparation was allowed to crystallize overnight in the cold. P and p pilus crystals were pelleted at 12K rpm for 60 minutes, and the supernatant discarded. The pellets of crystalline pili were then solubilized by magnetic stirring for about 1 hour in 0.063M ethanolamine at pH 10.6-12, followed by standing in the cold overnight in solubilizing buffer. One liter of solubilizing buffer was used per 80-tray harvest batch. The solubilized preparation was clarified by centrifugation at 9,000 g for 60 minutes.

The cycle of crystallization/solubilization was repeated for a second time by measuring the exact volume of the clarified supernatant and adding crystalline ammonium sulfate to 20-30% saturation, slowly and with stirring. The preparation was allowed to stand in the cold overnight, then centrifuged at 9,000 g to pellet the pilus crystals. The same sequences as before were repeated for solubilization and clarification.

The third cycle of purification was the same as the second, except that the ammonium sulfate concentration was reduced. All preparations were monitored by darkfield microscopy and SDS-PAGE throughout the purification procedure.

Bulk Vaccine Preparation

A composition comprising the purified pili in the desired proportions is taken up in 0.063 molar ethanolamine, diluted to 0.5 mg/ml and prefiltered once through a 45 mμ Gelman filter using a 142 mm milipore disk filtration unit with 2 liter capacity cylinder. Merthiolate is added to a final concentration of 0.01% and the final vaccine material then filter sterilized (0.45μ filter) and dialyzed to remove the ethanolamine buffer. The dialysis is carried out against phosphate buffer of 0.004M at pH 7-7.4. This dialysis procedure will cause precipitation of pili belonging to the P and p families. However, these precipitates are so finely divided that no problem is caused thereby.

The pili of the P and p families which are prepared in accordance with the foregoing procedure include pili prepared from the following strains:

P family: 46056, 28418, 13773, C8, 31920 (ATCC: 53501, 53504, 53505, 53503, 53502)

p family: 1910, 750 (ATCC:53499, 53500).

EXAMPLE IV

Final Preparation of Vaccine

Concentrations of the solutions or suspensions of pili produced as above are combined to provide from at least one member of each pilus family to up to 8 Type 1, 4P and 2 p subgroup pili to the total pilus concentration of about mg/ml.

We claim:

1. A method of protecting subjects against UTI caused by piliated *E. coli* organisms which comprises administering to a subject in need of protection, a composition capable of raising the antibody level of the subject to a level sufficient to provide such protection, comprising:

whole *E. coli* pili, designated vaccine pili, previously separated from other *E. coli* organism components, said composition comprising vaccine pili of at least three types, at least one of said types being selected from each of three pilus families designated "Type 1", "P" and "p", said vaccine pili being agglutinable by antisera derived from pili of at least one strain within each of the following families:

Type 1 family: B9, Bam, Rd, TD, H/T-1, 51, Br (ATCC:31702, 67053, 53507, 53498, 31705, 53508, 53506)

P family: 46056, 28418, 13774, C8, 31920 (ATCC:53501, 53504, 53505, 53503, 53502)

p family: 1910, 750 (ATCC:53499, 53500),

2. A method of claim 1 wherein the vaccine composition comprises pili agglutinable by antisera derived from pili derived from organisms of the strains ATCC 67053, 53502 and 53499.

3. A method of claim 1 wherein the vaccine composition comprises pili agglutinable by antisera derived from pili derived from organisms of each of the strains named in claim 1.

4. A method of claim 1 wherein the vaccine composition comprises pili derived from organisms of each of the strains named in claim 1.

5. A method of claim 1 wherein the vaccine composition is administered at least once to the subjects between about 5 and about 60 days before infection.

6. A method of claim 1 wherein there is administered between 1 and 100 ug./Kg body weight of the pilic component of the vaccine composition.

7. A vaccine for protecting subjects against UTI caused by piliated *E. coli* organisms which comprises a pharmaceutically acceptable carrier and whole *E. coli* pili, designated vaccine pili, previously separated from other *E. coli* organism components, in an amount capable of raising the antibody level of the subject to a level sufficient to provide such protection, said vaccine pili comprising pili of at least three types, at least one of said types being selected from each of three pilus families designated "Type 1", "P" and "p", said vaccine pili being agglutinable by antisera derived from pili, of at least one strain within each of the following families:
- Type 1 family: B9, Bam, Rd, TD, H/T-1, 51 Br (ATCC:31702, 6703, 53507, 53498, 31705, 53508, 53506)
- P family: 46056, 28418, 13774, C8, 31920 (ATCC:53501, 53504, 53505, 53503, 53502)
- p family: 1910, 750 (ATCC:53499, 53500)

8. A vaccine of claim 7 comprising pili agglutinable by antisera derived from pili derived from organisms of the strains ATCC 67053, 53502 and 53499.

9. A vaccine of claim 7 comprising pili agglutinable by antisera derived from pili derived from organisms of each of the strains named in claim 7.

10. A vaccine of claim 7 comprising pili derived from organisms of each of the strains named in claim 7.

* * * * *